Sept. 6, 1966 A. J. PORTER Plant Pat. 2,667
CRAB APPLE TREE
Filed Sept. 14, 1965
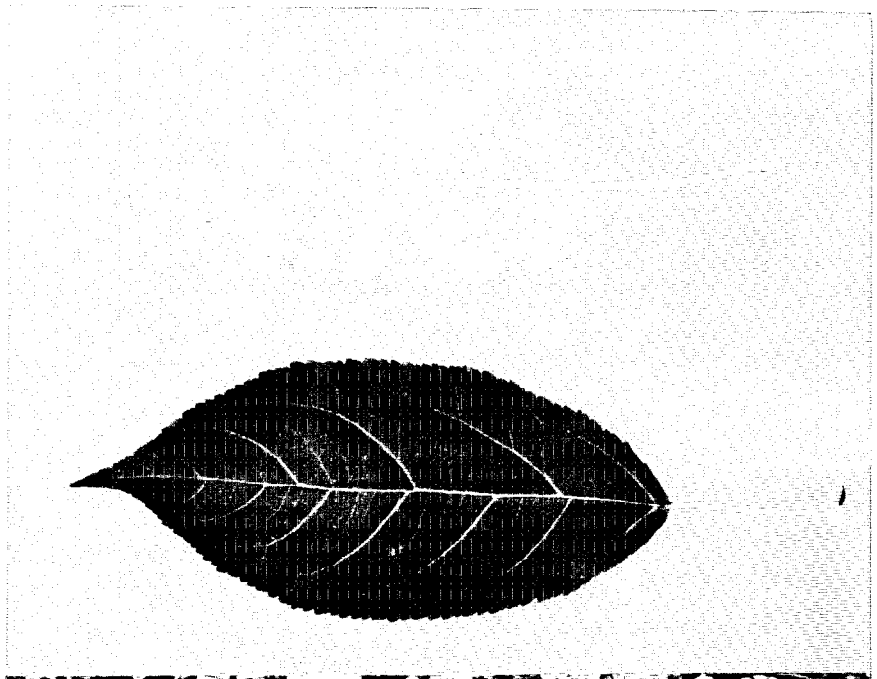
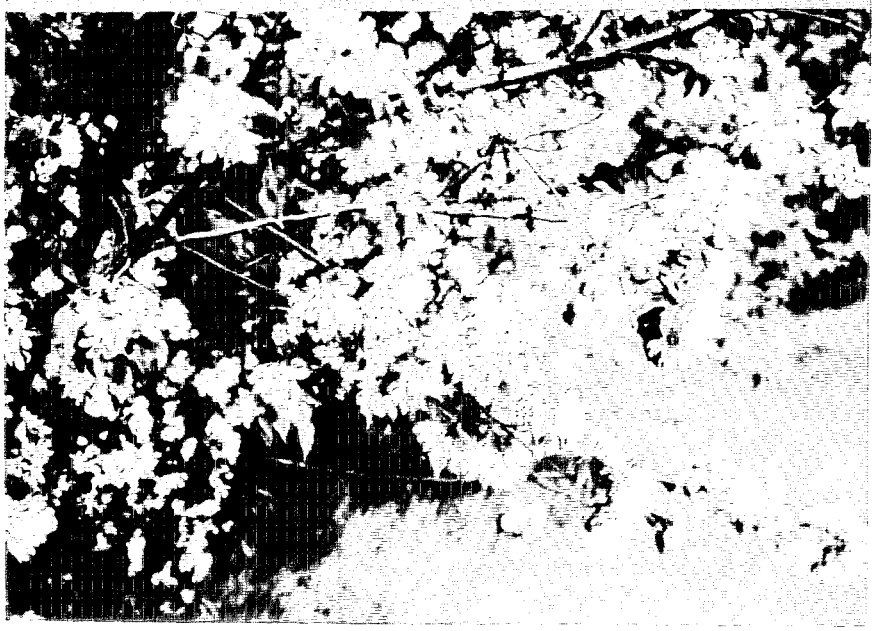
Inventor.
Albert J. Porter
By: Robb & Robb
Attorneys.

United States Patent Office

Plant Pat. 2,667
Patented Sept. 6, 1966

2,667
CRAB APPLE TREE

Albert J. Porter, Parkside, Saskatchewan, Canada, assignor to Inter-State Nurseries, Inc., Hamburg, Iowa, a corporation of Delaware

Filed Sept. 14, 1965, Ser. No. 487,345
1 Claim. (Cl. Plt.—34)

The present invention relates to a new and distinct variety of crab apple tree, which was discovered by me as an open-pollinated "Dolgo" seedling planted by me on my cultivated property near Parkside, Saskatchewan, Canada.

At the time of my discovery aforesaid, I noticed that one tree in a hedge row of unpatented "Dolgo" seedlings which I had planted, bloomed profusely but never set any fruit. I carefully preserved this tree and kept it under close observation for a period of years until I was convinced that the tree definitely was sterile, and therefore especially suitable for public plantings because it would not attract children like the usual fruiting crab apple trees, and would not litter parks, streets and boulevards with fallen fruit which normally make the grass unsightly in such public areas.

Further observations and tests of the original seedling and of asexual reproductions thereof as propagated for me by grafting in the nurseries of my assignee at Hamburg, Iowa, U.S.A., have established that my new seedling comes true and is distinct from all other crab apple varieties, as evidenced by the following unique combination of characteristics which are outstanding therein:

(1) Vigorous and hardy habits of growth;

(2) Relative freedom from fire blight common to other varieties;

(3) A prolific annual blooming habit;

(4) Attractive and relatively large white flowers which create a highly ornamental effect especially suitable for public plantings; and (5) A sterile habit which minimize its attractiveness to children because of the complete absence of fruit and also eliminates litter attributed to fallen fruit.

The accompanying drawing shows typical specimens of the flowers, foliage and branches of my new crab apple variety as depicted in color as nearly true as it is reasonably possible to make the same in an illustration of this character.

The following is a detailed description of my new crab apple variety, with color terminology in accordance with Koster's Color Guide, except where color terms of ordinary dictionary significance are obvious, as based on observations of specimens grown near Parkside, Saskatchewan, Canada:

Parentage: An open pollinated "Dolgo" seedling.
Tree: Medium size; upright; tall; dense; hardy.

*Trunk.*—Midway between slender and stocky; smooth.

*Branches.*—Slender; smooth. Color—Dull Greenish.

*Lenticels.*—Numerous.

*Leaves.*—Quantity—abundant. Length—3½ inches. Width—1⅝ inches. Shape—elliptical. Color: Upper side—near Holly Green, Plate 82; under side—near Lettuce Green, Plate 74. Margin—crenate. Petiole—long; up to 1¾ inches. Glands—none. Stipules—fine and almost hair-like; often none, but sometimes only one, and occasionally 2.

Flower buds:

*Hardiness.*—Hardy to 50° F. below zero, as grown near Parkside, Saskatchewan, Canada.

*Size.*—Small.

*Shape.*—Pointed.

*Color.*—White when opening; brownish green when dormant.

Flowers:

*Dates of first and full bloom.*—May 28 and June 3, respectively, annually at Parkside, Saskatchewan, Canada.

*Quantity.*—Abundant.

*Size.*—From medium to large.

*Petalage.*—Number of petals—5. Shape of petals—oval. Size of petals: Length—½ inch; width—¼ inch.

*Color.*—White.

Disease resistance: Excellent resistance to fire blight, as determined by comparison with other varieties which showed severe injury from fire blight when grown in the same row under the same conditions near Parkside, Saskatchewan, Canada.

I claim:

A new and distinct variety of crab apple tree, substantially as herein shown and described, characterized particularly as to novelty by its vigorous and hardy habits of growth, relative freedom from fire blight common to other varieties, a prolific annual blooming habit, attractive and relatively large white flowers which create a highly ornamental effect especially suitable for public plantings, and a sterile habit which minimizes its attractiveness to children because of the complete absence of fruit and also eliminates litter attributed to fallen fruit.

No references cited.

ABRAHAM G. STONE, *Primary Examiner.*
R. E. BAGWILL, *Assistant Examiner.*